United States Patent [19]

Patino et al.

[11] 4,007,259
[45] * Feb. 8, 1977

[54] DENTAL CREAM

[75] Inventors: Armando Patino, Mexico City; Bernardo Maldonado, Cd. Satelite Edo, both of Mexico

[73] Assignee: Colgate-Palmolive Company, New York, N.Y.

[*] Notice: The portion of the term of this patent subsequent to Jan. 16, 1990, has been disclaimed.

[22] Filed: Apr. 25, 1975

[21] Appl. No.: 571,825

Related U.S. Application Data

[60] Division of Ser. No. 412,444, Nov. 2, 1973, Pat. No. 3,711,604, which is a continuation of Ser. No. 256,309, May 24, 1972, abandoned.

[52] U.S. Cl. .................................. 424/49
[51] Int. Cl.$^2$ ......................... A61K 7/16
[58] Field of Search ................ 424/49–58; 260/37 R

[56] References Cited

UNITED STATES PATENTS

| | | | |
|---|---|---|---|
| 3,574,823 | 4/1971 | Roberts et al. | 424/49 |
| 3,711,604 | 1/1973 | Colodney et al. | 424/52 |
| 3,767,791 | 4/1974 | Cordon et al. | 424/49 |

FOREIGN PATENTS OR APPLICATIONS

| | | | |
|---|---|---|---|
| 2,031,676 | 1/1971 | Germany | 424/49 |

OTHER PUBLICATIONS

Bennett, Industrial Waxes, vol. II, published by Chemical Publishing Co., N.Y., 1963, p. 247.

*Primary Examiner*—Shep K. Rose
*Attorney, Agent, or Firm*—Steven J. Baron; Murray M. Grill; Herbert S. Sylvester

[57] ABSTRACT

A dental cream or toothpaste having dispersed therein particles of a water-insoluble thermoplastic polymeric material that are (a) visible because of their size and contrasting appearance, (b) substantially insoluble in the toothpaste base and (c) impalpable in the mouth during brushing of the teeth.

A speckled toothpaste having dispersed therein particles of a blend of water-insoluble thermoplastic material and pigment that (a) are visible because of their size and contrasting appearance, (b) are substantially insoluble in the toothpaste base, (c) are impalpable in the mouth during brushing of the teeth and (d) have below 5% pigment concentration and a ratio of thermoplastic material to pigment of at least 20:1.

A toothpaste comprising a clear gel base having dispersed therein a dental polishing agent having substantially the same refractive index as the clear gel base and visible particles of water-insoluble thermoplstic material contrasting with the gel base.

10 Claims, No Drawings

DENTAL CREAM

This is a divisional, of application Ser. No. 412,444 filed Nov. 2, 1973, now U.S. Pat. No. 3,711,604 which is a continuation of Ser. No. 256,309 5/24/72 abandoned.

The invention relates to aesthetically pleasing toothpaste formulations containing dispersed particles that are individually visible to the unaided eye. More specifically, the invention provides a clear, opaque or translucent toothpaste having dispersed therein macroscopically visible particles that contrast with the toothpaste base to provide a speckled effect. The invention makes it possible to provide a highly stable speckled toothpaste having a desirable, pleasant feel in the mouth during brushing, good brushing characteristics, good cleaning power, a distinct and brilliant speckled effect with a sharp and stable contrast between the speckles and the toothpaste base.

The materials useful in producing the colored particles incorporated in the toothpaste formulations of this invention include the broad class of water-insoluble non-abrasive polymeric materials classifiable as a thermoplastic. Representative of such materials are synthetic polymers which are in the categories of polyolefins, e.g. polyethylene and polypropylene; polyvinyl chloride copolymers of polyvinyl chloride and polyvinyl alcohol, vinyl acetate and vinylidene chloride; polyvinyl acetate; alkyl methacrylates e.g., polyisobutyl methacrylate; polystyrene, polymethyl styrene; synthetic rubbers, such as styrenebutadiene copolymers; polyamides, such as nylon; polyacrylates; cellulosics, such as acetates and butyrates; polycarbonates; phenoxys, such as polymers of bis-phenol-A and epichlorohydrin; and mixtures of said materials.

Particularly suitable thermoplastic materials or polymers for use in this invention usually have a molecular weight between about 1000 and 20,000. Best results have thus far been obtained with materials whose molecular weights are below 10,000, and have a hardness value expressed as tenths of a millimeter needle penetration (100 grams/5 sec/25° C, ASTM DI-1321) between about 1 and 15 although harder or softer materials may be used if not objectionable in the final toothpaste. The polymers may be prepared, for instance, by suspension, bulk, and emulsion polymerization methods which are well known in the art.

The following table lists preferred synthetic thermoplastic polymeric materials and their properties. Polyethylenes having a molecular weight from about 1,000 to 5,000 are particularly compatible and inert in the toothpaste base and impalpable in the mouth during brushing and are preferred materials.

| Resin | A.M.W.[1] | S.P.[2] Approx. | Hardness[3] | S.G.[4] | A.V. CP[5] | |
|---|---|---|---|---|---|---|
| poly-ethylene[6] | 2,000 | 105° C. | 3.5 | 0.92 | 200 | (140° C) |
| " | 2,200 | 107° C. | 3.0 | 0.92 | 220 | " |
| " | 3,500 | 116° C. | 1.0 | 0.93 | 350 | " |
| " | 5,000 | 109° C. | 2.5 | 0.92 | 4000 | " |
| " | 1,500 | 102° C. | 7.5 | 0.91 | 145 | " |
| " | 1,100 | 195° C. | 80.0 | 0.89 | 40 | " |
| " | 2,000 | 96° C. | 9.5 | 0.91 | 230 | " |
| " | 3,500 | 204° C. | 7.0 | 0.92 | 500 | " |
| oxidized "[7] | 1,800 | 104° C. | 4.0 | 0.94 | 320 | (125° C) |
| " " | 3,000 | 106° C. | 3.0 | 0.94 | 1200 | " |
| Polyamide[8] | 6,000-9,000 | 110° C. | 4 | 0.98 | 2200 | " |
| " | " | 95° C. | 15 | 0.98 | 1100 | " |
| " | " | 110° C. | 3 | 0.98 | 3800 | " |
| Alpha methyl Styrene -vinyl toluene copolymer[9] | 1,000 | 100° C. | — | — | 3500 | (140° C) |

[1]Average Molecular Weight
[2]Softening Point (Approx.) ASTM E-28
[3]0.1 mm needle penetration ASTM DI-1321 (100 grams/5 sec/25° C)
[4]Specific Gravity
[5]Average Viscosity CP
[6]Available from Allied Chemical Company under the trademark A-C polyethylene grades 6, 6A, 7, 7A, 8, 8A, 615, 617, 617A, G-201 and 400.
[7]Available from Eastman Chemical Products, Kingsport, Tenn. under the trademark EPOLENE. These materials are emulsifiable and have both an acid value and saponification number of 9-10. Similar materials are available from Allied Chemical Company under the trademark A-C polyethylene grades 656, 629, 655 and 680.
[8]Produced from ethylene diamine in accordance with U.S. Pat. No. 2,379,413. Available from the Chemical Division of General Mills Co., Kankakee, Ill. under the trademark Versamid grade 930, 940 and 950.
[9]Available from Picco Resin Company, Clairton, Pa., under the trademark Piccotex 100.

The foregoing materials are non-toxic, substantially insoluble in the toothpaste base and in water and do not attack the material from which the packing tube for the dental cream is constructed (usually aluminum or lead). As supplied, they are generally uncolored, e.g., water-white or cloudy. Particles made from these materials are of a macroscopically visible size having a mean diameter of at least about 150 microns and generally below 800 microns, usually below 600 microns, preferably between 150 and 420 microns, and are substantially impalpable in the oral cavity during use.

The macroscopically visible particles of the invention preferably contrast with the toothpaste base. Typically the toothpaste base itself is white, opaque, clear or translucent. The visible particles may be of any desired color that would be visible against the dental cream background depending on the specific aesthetic effect desired. In a preferred form of the invention the particles contain dispersed coloring agent in amount of well below 10% and preferably less than about 5%, e.g., particularly in the range of about 0.1 to about 1 or 2%, such as about 0.3 to 0.6%. The ratio of the amount of thermoplastic polymeric material to the amount of dispersed coloring agent is preferably well above 10:1, more preferably greater than 20:1, and still more preferably above about 40:1, e.g. about 100:1 to 300:1. The use of such small proportions and high ratios yields speckles of excellent contrasting color and exceptional color stability and bleed resistance, even with pigments (such as the lakes mentioned below, which are formed from water-soluble dyes bound to an insoluble substrate) which otherwise have a tendency to bleed into the toothpaste on long standing, particularly when the toothpaste base contains water-insoluble, ether-miscible liquid solvents such as chloroform. In this aspect of the invention one may also employ in place of or in admixture with the polymeric material, a water-insoluble waxy material such as carnauba wax. Also, for best bleed-resistance it is preferable to avoid diluting the visible particles by the presence therein of a major proportion, particularly not substantially above about 30%, of non-thermoplastic particles such as dispersed, fine particles of dental polishing agent. The incorporation in the colored visible particles of a minor amount, e.g., about 5 to 30%, preferably about 10 to 20% of such polishing agent, e.g., particles of dicalcium phosphate of a size and grade known to be suitable for use as a polishing agent in toothpaste, has yielded speckled toothpastes of excellent appearance and stability.

Typically, the amount of colored thermoplastic particles in the toothpaste formulations of the invention is below 10% and generally much less, e.g. less than 5%, such as about 0.2 percent to about 1 percent by weight, preferably about one-half percent e.g., 0.4 percent. However, it should be recognized that the amount of particles present can be varied beyond this range depending on the speckled effect desired in the final formulation.

In accordance with one aspect of the invention, pigments such as the metallic lakes of suitable dyes can be used to color the thermoplastic particles of the invention. A pigment is generally defined as a finely powdered insoluble colored material that is dispersed and suspended, as opposed to being dissolved, in the medium to be colored. The pigment may be entirely of a single insoluble colored material (such as ultramarine blue) or it may be composed of a combination of a water-soluble dye and a water-insoluble carrier to which the dye is bound. Typical of the latter materials are the well known "lakes" wherein the carrier material is a metallic oxide such as alumina.

Since the colored particles of the invention are used in dental cream formulations the pigments utilized should be suitable for use in the oral cavity. Suitable pigments include ultramarine blues and pinks, cosmetic green oxide, cosmetic red oxide, carbon black, ferric oxides, pigment red No. 5 color index 12,490, pigment blue No. 27 color index 77,510, and pigment green No. 7 color index 74,260. Further suitable pigments are those referred to in the U.S. as FD&C (food drug and cosmetics) and D&C (drugs and cosmetics) approved pigments. Typical of pigments of this type are metallic lakes of the following D&C dyes:

| Color | Color Index No. |
|---|---|
| D&C Green No. 5 | 61570 |
| D&C Green No. 6 | 61565 |
| D&C Green No. 8 | 59040 |
| D&C Yellow No. 10 | 47005 |
| D&C Red No. 6 | 15850 |
| D&C Red No. 7 | 15850 |
| D&C Red No. 8 | 15585 |
| D&C Red No. 9 | 15585 |
| D&C Red No. 10 | 15630 |
| D&C Red No. 11 | 15630 |
| D&C Red No. 12 | 15630 |
| D&C Red No. 13 | 15630 |
| D&C Red No. 19 | 45170 |
| D&C Red No. 21 | 45380A |
| D&C Red No. 22 | 45380 |
| D&C Red No. 27 | 45410 |
| D&C Red No. 28 | 45410 |
| D&C Red No. 30 | 73360 |
| D&C Red No. 33 | 17200 |
| D&C Red No. 34 | 15880 |
| D&C Red No. 36 | 12085 |
| D&C Red No. 37 | 45170B |
| D&C Orange No. 5 | 45370A |
| D&C Orange No. 10 | 45425A |
| D&C Orange No. 11 | 4542Na |
| D&C Orange No. 17 | 12075 |
| D&C Blue No. 1 | 42090 |
| D&C Blue No. 4 | 42090 |
| D&C Blue No. 6 | 73000 |
| D&C Blue No. 9 | 69825 |

Lakes are discussed in the "Encyclopedia of Chemical Technology" edited by Kirk and Othmer (e.g. in the first edition, Vol. 2, pages 262-263) and in Jennison "Manufacture of Lake Pigments from Artificial Colors" (e.g. in the 2nd. edition published 1920 by Scott, Greenwood, London).

In accordance with one aspect of the invention, suitably colored thermoplastic particles can be produced by first heating the thermoplastic material until it is molten and then mixing suitable pigment into the molten mass. After the pigment is added and uniformly dispersed, the molten mixture is solidified by pouring it onto and passing it through a water cooled roll mill. The solidified thermoplastic which is usually in film form can then be broken up into chips, ground to particulate form and screened to isolate the desired size particles.

The toothpaste base includes liquids and solids that are proportioned to form a creamy mass of desired consistency which is extrudable from an aerosol container or a collapsible tube (whose walls are for example fabricated from aluminum or lead). In general, the liquids in the dental cream will comprise chiefly water, and water-soluble, non-volatile liquids such as humectants e.g. glycerine, aqueous solutions of sorbitol, propylene glycol, polyethylene glycol 400, etc. including suitable mixtures thereof. It is advantageous usually to use a mixture of both water and a humectant or binder such as glycerine or sorbitol. The total liquid content will generally be about 20 to 75 percent by weight of the formulation. It is preferred to use also a gelling agent in dental creams such as the natural and synthetic gums and gum-like materials, for example, Irish moss, gum tragacanth, methyl cellulose, polyvinylpyrolidone, and starch usually in an amount up to about 10 percent, preferably about 0.2 to 5 percent, by weight of the formulation. Inorganic gelling agents can be employed, such as synthetic silicated clays having the formula $[Si_8Mg_{5.1} Li_{0.6} H_{7.6}O_{24}]^{0.6-}Na0.6^+$ and available under the trademark Laponite CP and Laponite SP. The synthetic silicated clays are particularly suitable for use in formulating a transparent toothpaste base.

The new formulation typically includes a dentally acceptable polishing agent of the type employed in dental creams. Representative polishing agents include, for example, dicalcium phosphate, tricalcium phosphate, insoluble sodium metaphosphate, aluminum hydroxide including hydrated alumina, colloidal silica, magnesium carbonate, calcium carbonate, calcium pyrophosphate, bentonite, etc. including suitable mixtures thereof. It is preferred to use the water insoluble phosphate salts as the polishing agent and more particularly insoluble sodium metaphosphate and/or a calcium phosphate such as dicalcium phosphate dihydrate.

When the toothpaste is to be visually clear, a polishing agent having a refractive index about the same as the refractive index of the gel base i.e., from about 1.4 to 1.5, can be used. Suitable polishing agents for use in clear toothpaste bases are colloidal silica, such as the silica xerogels and alkali metal aluminosilicate complexes. The foregoing polishing agents all have a refractive index between about 1.44 and 1.48 and are substantially invisible when incorporated into a clear gel toothpaste base. The polishing agent is generally present in amounts from about 20 to 75 percent by weight. In a visually clear base the amount of polishing agent is generally from about 5 to 50 percent by weight.

Suitable silica xerogels are synthetic, aggregated, amorphous, porous silica materials having an average particle diameter of between about 2 and 20 microns, preferably between about 3 and 15 microns, and, generally, a surface area of at least about 300, and up to about 600 to 800 square meters per gram. A suitable silica xerogel is available from Grace Davison Chemical Company under the trade name Syloid 63. The material has an average particle diameter of about 8–10 microns. Other suitable silica xerogels include Syloid 65 (average particle diameter of about 5 microns), Syloid 73 (average particle diameter of about 5 microns), and Syloid 72 and 74, all of which are available from the Grace Davison Chemical Company. The silica xerogels typically have a refractive index of about 1.46. Other suitable silica materials are available from the Monsanto Chemical Company under the trademark Santocel and Santocel 100.

The abrasive material used in the clear gel vehicle of the toothpaste formulations of the invention can be a water insoluble complex metallic salt of aluminosilicate having a refractive index close to that of the gel vehicle. Representative of such materials are synthetic amorphous complex aluminosilicate salts of an alkali metal or alkaline earth metal in which silica is interbonded with alumina and which contains up to 3.3% by weight of the polishing agent of alumina, and in which the mole ratio of silica to alumina is at least about 45:1. The foregoing alumino silicate abrasives have a refractive index between about 1.44 – 1.47 and include up to about 20% by weight of moisture and up to about 10% by weight of alkali metal or alkaline earth metal oxide.

The complex aluminosilicate salt described above is typically a sodium or calcium salt, and forms a particularly desirable product. It is an amorphous powder which further has the property of being invisible when incorporated in a clear gel dental vehicle. Thus, a suitable particle size for the polishing ingredient is up to about 40 microns, preferably about 1–20 microns. The typical moisture content, measured by loss on ignition is about 5–20% by weight of the polishing ingredient and the typical content of alkali metal oxide such as sodium oxide or alkaline earth metal oxide such a calcium oxide is up to about 10%, generally about 0.3–2%, by weight. Typically, the agent has a loose bulk density of up to about 0.2g/cc, preferably about 0.07–0.12g/cc.

Organic surface-active agents are used in toothpaste compositions to assist in achieving thorough and complete dispersion of the composition throughout the oral cavity and to render them more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulfonates, such as the sodium salt of the monosulfonated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbon atoms in the fatty acid, alkyl, or acyl radicals, and the like and combinations of any of the foregoing materials. Examples of the last mentioned amides are N-lauroyl sarcosine, and the sodium, potassium, and ethanol-amine salts of N-lauroyl, N-myristoyl, or N-palmitoyl sarcosine. The use of these sarcosinate compounds in dentifrice compositions is particularly advantageous since these materials exhibit a prolonged and marked effect in the inhibition of acid formation in the oral cavity due to carbohydrate breakdown in addition to exerting some reduction in the solubility of tooth enamel in acid solutions. Preferably they are substantially free from soap or similar higher fatty acid material which tends to reduce their effect.

Other particularly suitable surface active materials include nonionic agents such as condensates of sorbitan monostearate with approximately 60 moles of ethylene oxide, condensates of ethylene oxide with propylene oxide, condensates of propylene glycol ("Pluronics") and amphoteric agents such as quaternized imidazole derivatives which are available under the trademark "Miranol" such as Miranol $C_2M$.

Various other materials may be incorporated in the opaque and clear toothpaste formulations of this invention. Examples thereof are coloring or whitening agents or dyestuffs, including water soluble dyes such as FD&C and D&C colors, preservatives, silicones, chlorophyll compounds, ammoniated materials such as urea, diammoniumphosphate and mixtures thereof, and other constituents. These adjuvants are incorporated in the formulation in amounts which do not substantially adversely affect the properties and characteristics desired and are selected and used in proper amount depending upon the particular type of preparation involved.

The dental cream formulations can also include a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2$-KF), potassium fluorozirconate, sodium hexafluorostannate, stannous chlorofluoride, and sodium monofluorophosphate. These materials, which dissociate or release fluorine-containing ions, suitably may be present in an effective but non-toxic amount, usually within the range of about 0.1 to 1% by weight, based on the water-soluble fluorine content thereof. Sodium fluoride, stannous fluoride, and sodium monofluorophosphate are particularly preferred as well as mixtures thereof.

Antibacterial agents may also be employed in the oral preparations of the instant invention to provide a total content of such agents of up to about 5% by weight. Typical antibacterial agents include $N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
1,6-Di-P-Chlorophenyl Biguanidohexane;
1,6 bis (2,Ethylhexyl Biguanido) hexane;
5-amino-1, 3-bis (2-ethylhexyl)-5-methylhexahydro pyrimidine;
and their non-toxic acid addition salts.

Synthetic finely divided pyrogenic silica such as those sold under the trademark Cab-o-Sil M-5, Syloid 244, Syloid 266 and Aerosil D-200 may also be employed in amounts of about 1-5% by weight particularly to promote thickening or gelling and to improve clarity of the dentifrice.

The taste of the toothpaste formulations may be modified by employing suitable flavoring or sweetening materials. Examples of suitable flavoring constituents include the flavoring oils, e.g. oils of spearmint, peppermint, cinnamon, lemon and orange as well as sodium methylsalicylate. Suitable sweetening agents include sucrose, lactose, maltose, sorbitol, sodium cyclamate, perillartine and saccharine. Suitably, flavor and sweetening agent may together comprise from about 0.01 to 5% or more of the compositions of the invention. The toothpaste formulations can be provided with the unusual, biting flavor of chloroform. Accordingly, instead of or in addition to the foregoing flavoring or sweetening materials up to about 5%, usually greater than 1% and preferably between 1 and 5% by weight chloroform (or chloroform flavoring) can be included in the dental cream formulations of the invention.

According to a specific aspect of the invention the new colored thermoplastic particles can be incorporated into a toothpaste base containing chloroform without dissolving, disintergrating or bleeding color. The preferred color thermoplastic particles of the invention are substantially inert in chloroform and chloroform containing toothpaste. When suspended in chloroform at room temperature, preferred color thermoplastic particles according to the invention maintain their integrity after 16 hours and do not discolor the chloroform. Similarly, when incorporated in a toothpaste containing about 3 percent chloroform and maintained at 120° F. for 12 weeks, the preferred colored thermoplastic particles remained discrete and did not noticeably discolor the toothpaste base.

It is desirable to adjust the pH of the dental cream formulations to the range of about 3 to 9 using such acids as citric, acetic, chloropropionic, malonic, formic, fumaric, methoxyacetic, and propionic. Lower values of pH than 3 are generally undesirable for oral use. When stannous ions are present, the pH is preferably lower than about 5. The preferred pH range is 3.5 to about 5.0 when stannous ions are present and about 4.5 to about 7.0 in the absence of stannous ions.

The following specific examples are further illustrative of the nature of the present invention but it is understood that the invention is not limited thereto. Dental cream formulations are prepared in the usual manner, except as indicated, and all amounts and proportions are by weight except as otherwise indicated.

EXAMPLE 1

Colored thermoplastic particles suitable for incorporation into either opaque or clear gel type dental cream formulations are prepared in accordance with the following procedure.

In this Example there is employed a non-emulsifiable grade of polyethylene, having the following properties:

| | |
|---|---|
| Molecular weight | approx. 1500 |
| Softening point (ASTM E-28) | 120° C. |
| Hardness (0.1mm) (ASTM DI-1321) | 7.5 |
| Density g/cc (ASTM D-1505) | 0.91 |
| Viscosity cps. | 140° C. |
| Brookfield | 145 |

This polyethylene is resistant to such liquids as ethyl alcohol, water and aqueous 50% sodium hydroxide; when exposed to an excess of such liquids it absorbs less than 2%, and generally less than about 1%, of the liquid; it is attacked, however, by such liquids as carbon tetrachloride and toluene.

99.6 parts of the foregoing polyethylene material are heated until molten (about 105° to 110° C) in a suitable vessel having agitator means. 0.4 part of D&C Blue No. 1 aluminum lake, color index 42090 is then added to, and thoroughly mixed with, the molten plastic while the temperature is maintained between about 105° and 110° C. The molten mixture is then poured onto a roll mill including three internally water cooled rollers spaced 1/32 inch apart, to obtain a film of the colored polyethylene material. The colored polyethylene film is cooled to about 50° C. during the milling process and is then broken up into chips. The chips are fed to a solid granulator and are ground to particulate form. The solids granulator can be a double roll mill with grooves or a Stokes type granulator with a mesh and rotor. The particulate material is then fed to a sifter having a number 40 mesh (U.S. sieve series) screen and a number 45 mesh (U.S. sieve series) screen. The particles retained on the number 40 mesh screen are recycled to the solids granulator for further size reduction and those that pass through the number 45 mesh screen are recycled to the heating-mixing vessel to be remelted. The particles that pass through the 40 mesh screen and are retained on the 45 mesh screen are utilized in the dentifrice formulations of the invention. They are characterized by having an aesthetically pleasing and vivid blue color, an irregular shape, and a particle size of about 350 to about 420 microns.

EXAMPLE 2

A white, opaque dental cream having the following composition is formulated by the usual technique.

| Components | Parts |
|---|---|
| Glycerine | 25.63 |
| Tetra Sodium Pyrophosphate | 0.24 |
| Sodium carboxymethylcellulose | 0.74 |
| Saccharin, sodium | 0.19 |
| Sodium benzoate | 0.49 |
| Deionized water, irradiated | 14.57 |
| Calcium carbonate | 4.97 |
| Dicalcium phosphate | 46.14 |
| Sodium lauryl sulfate (dental grade) | 0.97 |
| Sodium N-lauroyl sarcosinate | 0.71 |

0.40 parts of the colored particles of Example 1 are added to the above formulation and the mixture of cream and particles is thoroughly mixed to uniformly disperse the particles. After the particles are uniformly incorporated into the dental cream 1.29 parts of toothpaste flavoring and 3.58 parts of chloroform can be thoroughly blended into the mixture. The chloroform and flavoring additives provide a pleasant, stimulating and biting taste to the dental cream.

The dental cream formulated in accordance with this example can be packaged in unlined aluminum tubes and has an attractive appearance and stimulating taste. The dispersed colored particles do not settle appreciably during normal shelf life, they are not attacked by the chloroform, e.g., they do not dissolve or bleed color into the toothpaste base, and are impalpable in the oral cavity during use.

EXAMPLE 3

The following opaque dentifrice is prepared:

| Components | Parts |
|---|---|
| Glycerine | 20.0 |
| Hydroxyethylcellulose | 1.2 |
| Hydrated alumina | 52 |
| Sodium N-lauroyl sarcosinate | 2.0 |
| Sodium saccharin | 0.2 |
| Flavor (peppermint) | 1.0 |
| Deionized water (irradiated) | 20 |

0.5 parts of the colored plastic particles of Example 1 are thoroughly dispersed in this formulation to produce an aesthetically attractive speckled dental cream.

EXAMPLE 4

The following visually clear dentifrice is prepared:

| Components | Parts |
|---|---|
| Sorbitol (70% aqueous solution) | 75.0 |
| Glycerine | 25.0 |
| Laponite SP | 2.0 |
| Sodium N-lauroyl sarcosinate | 2.0 |
| Sodium saccharin | 0.1 |
| Aerosil D200 | 3.0 |
| Soldium aluminosilicate | 16.0 |
| Flavor | 1.0 |
| Color (water soluble dye) | 1.0 |
| Water | 20.0 |

1 part by weight of the colored particles of Example 1 are thoroughly dispersed in the formulation to produce an aesthetically attractive clear gel dentifrice.

The sodium aluminosilicate employed is a complex having a refractive index of 1.46, a moisture content of about 6 percent, an average particle size of about 35 microns and a sieve loose bulk density of about 0.07g/cc.

Other polymers having suitable properties comparable to the polyethylene resin may be selected, such as the types of polymeric materials previously described, including polyvinyl chloride resin, polymethyl methacrylate resin and polystyrene resin, and used similarly in such formulations in desired amount.

Although the foregoing examples include preferred and typical formulations, they should not be taken as limitations on the invention. Accordingly, reference should be made to the following claims in determining the full scope of the invention.

We claim:

1. A white opaque clear or translucent aqueous dental cream toothpaste containing at least about 1 up to about 5% by weight chloroform and having dispersed therein 0.2 to 10% by weight of particles of 10 to 300 parts of a water insoluble unpreflavored polymeric thermoplastic low molecular weight polyolefin, per part of dental cream contrasting pigments, or lakes, which otherwise have a tendency to bleed into chloroform containing toothpaste, and that are visible and substantially insoluble in the toothpaste base, being substantially inert to said chloroform, and said particles comprising water and chloroform insoluble pigmented but unflavored plastic subparticles of a desired contrasting color that are visible against the contrasting dental cream background, said chloroform being blended into the dental cream after the particles are first dispersed therein, thereby imparting bleed-resistance of said color in said toothpaste base, said speckles of pigmented plastic particles thereby retaining their distinct and contrasting appearance for at least the normal shelve life of the product and the time it takes to be used by the consumer, without significant attack by the chloroform of the pigment in the pigmented visible particles which would otherwise result in leaching or bleeding of the pigment from the particles into the contrasting color toothpaste base.

2. The toothpaste of claim 1 wherein the visible particles have a mean particle diameter between about 150 and 600 microns.

3. The toothpaste of either of claim 1 and 2 wherein the polymeric thermoplastic material has a molecular weight within the range of about 1,000 and 20,000.

4. The toothpaste of claim 3 wherein the polymeric thermoplastic material is polyethylene having a molecular weight between 1,000 and 5,000.

5. The toothpaste of any one of the preceding claims wherein the particles include from about 0.1 to 5 percent by weight of pigment.

6. The toothpaste of any one of the preceding claims containing from about 0.2 to 1.0 percent by weight of said particles.

7. The toothpaste of claim 1 including a visually clear toothpaste base.

8. The toothpaste of claim 7 wherein said visually clear toothpaste base includes particles of polishing agent having substantially the same refractive index as said toothpaste base.

9. The toothpaste of claim 1 wherein the hardness of the thermoplastic material measured as 0.1 mm penetration (100 grams/5sec/25° C.) is at least 1.

10. The toothpaste of claim 1 wherein the particles include up to 5 percent coloring material and when dispersed in chloroform at room temperature for 16 hours the particles do not significantly discolor the chloroform.

* * * * *